United States Patent [19]

Dröse et al.

[11] Patent Number: 5,856,548

[45] Date of Patent: Jan. 5, 1999

[54] PROCESS FOR PREPARING DIMETHYLMONOCHLOROSILANE

[75] Inventors: Jürgen Dröse; Wilfried Knott, both of Essen; Dirk Wolfgram, Bochum, all of Germany

[73] Assignee: Th. Goldschmidt AG, Essen, Germany

[21] Appl. No.: 69,634

[22] Filed: Apr. 29, 1998

[30] Foreign Application Priority Data

May 17, 1997 [DE] Germany .................. 197 20 890.8

[51] Int. Cl.$^6$ ...................................... C07F 7/08
[52] U.S. Cl. ............................................. 556/474
[58] Field of Search ............................... 556/474

[56] References Cited

U.S. PATENT DOCUMENTS 5,015,624  5/1991  Schulz ..................................... 556/474
5,455,367  10/1995  Klein et al. .............................. 556/474

Primary Examiner—Paul F. Shaver
Attorney, Agent, or Firm—Scully, Scott, Murphy & Presser

[57] ABSTRACT

The invention relates to a process for preparing dimethylmonochlorosilane $(CH_3)_2Si(H)Cl$ by partial hydrogenation of dimethyldichlorosilane $(CH_3)_2SiCl_2$ in a reaction system comprising magnesium hydride and aluminum chloride and an inert liquid organic vehicle while milling continually.

12 Claims, No Drawings

PROCESS FOR PREPARING DIMETHYLMONOCHLOROSILANE

FIELD OF THE INVENTION

The invention relates to a process for preparing dimethylmonochlorosilane $(CH_3)_2(H)Cl$ by partial hydrogenation of dimethyldichlorosilane $(CH_3)_2SiCl_2$ in a reaction system comprising magnesium hydride and aluminum chloride and an organic solvent while milling continually.

BACKGROUND OF THE INVENTION

Alkylhydrogenchlorosilanes are of great interest as starting materials in industrial organosilicon chemistry. By means of a combination of hydrosilylation and hydrolysis steps they open up a great variety of commercially interesting functionalized silicones.

Dimethylmonochlorosilane (DMMCS) and methyldichlorosilane are obtained as by-products of the Rochow synthesis and have to be separated from the main product dimethyldichlorosilane (DDS) (K. Schnurrbusch, Ullmanns Encylopädie der Technischem Chemie, Volume 15, Urban & Schwarzenberg-Verlag, pp. 748–769 (1964)). However, the direct synthesis which is optimized for high DDS yields is of only very limited usefulness as a source of the sought-after chlorohydrogensilanes.

A further route to dimethylmonochlorosilane is the catalytic dissociation of organochlorosilanes which are present in the residue from the direct synthesis (M. Wick, G. Kreis, F.-H. Kreuzer, Ullmanns Encylopädie der Technischen Chemie, Volume 2, 4th Edition, Verlag Chemie, pp. 485–508 (1982))).

The literature refers to many processes for converting DDS into DMMCS by means of metal hydrides. JP 89-158938 teaches a process for the partial hydrogenation of DDS using lithium hydride in an LiCl/KCl melt at from 355° C. to 470° C. with yields of from 8% to 17% of DMMCS being obtained. From the point of view of energy consumption, this process is not very attractive.

U.S. Pat. No. 4,115,426 describes the use of the reduction system $NaH/NaBH_4$ in hexamethylphosphoramide (HMPA) in a temperature range from 40° C. to 80° C., with dimethylmonochlorosilane being formed in a yield of 71%. The extremely carcinogenic HMPA restricts broad industrial utilization of this method.

Combination of calcium hydride $CaH_2$ and aluminum chloride or titanium hydride $TiH_2$ and aluminum chloride have been described for the partial hydrogenation of DDS; at 250° C. and 300° C. in an autoclave, these give variable mixtures of DDS, DMMCS, trimethylchlorosilane and methylchlorosilane plus gaseous by-products (J. Organomet. Chem. 206 (3), pp. 279–286 (1981)). The reaction times in this high-temperature process are very long and range from 17 to 90 hours.

Hengge et al. describes the possibility of preparing partially hydrogenated organosilicon halide compounds in a system comprising trialkylstannyl chloride/sodium hydride and diethylene glycol dialkyl ethers as solvent. The reaction, which proceeds even at room temperature, requires the catalytic addition of bipyridyl or $\lambda^3$-phosphorus compounds and gives, e.g. when using methyltrichlorosilane, a 55% yield of methylchlorosilane plus methylsilane and methyldichlorosilane.

DE-A-44 42 753 claims alkylhydrogenchlorosilanes of the type $R_{(4-n-m)}SiCl_nH_m$, obtainable by catalytic reaction of the corresponding alkylchlorosilanes $R_{(4-p)}SiCl_p$ with hydrogen in the gas phase at temperatures of from 100° C. to 600° C. and under superatmospheric pressure, using the metals nickel and/or ruthenium and/or rhodium and/or palladium and/or platinum as catalysts, either as such or in supported form. When using DDS, this process leads to mixtures comprising dimethylmonochlorosilane, methyldichlorosilane and trimethylchlorosilane, with maximum yields of 4.0% of dimethylmonochlorosilane at very low DDS conversations (from 3.9% to 14.8) and selectivities of from 27.2% to 40.8% being achieved. To obtain isolable amounts of target product, the process therefore requires a recirculation procedure which is expensive in terms of apparatus. The selective removal of the DMMCS already formed in the reaction matrix during passage through the reactor is particularly difficult.

In view of this prior art, it is therefore an object of the present invention to develop a process for the partial hydrogenation of dimethyldichlorosilane which is an advance in terms of economics, safety and yield.

DE-C-43 13 130 teaches a process for preparing silanes or organosilicon hydrides by reduction with a magnesium hydride in a liquid reaction medium, which comprises a combination of the following features:

Use of non-pyrophoric magnesium hydride, use of customary ethers as a reaction medium, continuous removal by means of mechanical energy or ultrasound of the magnesium halide which deposits on the surface of the magnesium hydride particles during the reaction, with the preferred feature being use of a magnesium hydride which has been prepared autocatalytically.

Nonpolar reaction media such as aliphatic or cycloaliphatic hydrocarbons are not suitable for preparing silanes or organosilicon hydrides according to this characteristic process (see Comparative Example 1, experiment on the reduction of dimethyldichlorosilane).

BRIEF SUMMARY OF THE INVENTION

It has now surprisingly been found that dimethyldichlorosilane can be reacted with $MgH_2$ under the action of milling energy in nonpolar reaction media to give silane mixtures having a high proportion of dimethylmonochlorosilane if an adequate amount of aluminum halide is added to the reaction system.

Thus, the invention comprises a process for preparing dimethylmonochlorosilane $(CH_3)_2Si(H)Cl$ comprising establishing a reaction mixture comprising dimethyldichlorosilane $(CH_3)_2SiCl_2$, magnesium hydride, and aluminum chloride in an inert liquid organic vehicle, and partially hydrogenating said dimethyldichlorosilane in said reaction mixture while milling continually in said liquid organic vehicle.

Use is advantageously made of a non-pyrophoric, autocatalytically prepared magnesium hydride which is prepared as described in DE-A-40 39 278 (the disclosure of which is hereby incorporated herein by reference) from finely divided magnesium by hydrogenation, with magnesium hydride having a particle size of $\leq 400\ \mu m$ being added as catalyst in an amount of at least 1.2% by weight, based on magnesium to be hydrogenated, and the hydrogenation being carried out at a temperature of $\geq 250°$ C. and a pressure of from 0.5 to 5.0 MPa while stirring the reaction mixture.

DETAILED DESCRIPTION OF THE INVENTION

According to the process of the invention, the reactants DDS and $MgH_2$ are reacted in molar ratios of from 10:0.5 to 1:1.5. The stoichiometry selected is preferably in the range from 1:0.8 to 1:1 so that, on the one hand, the reaction is accelerated by a high hydride concentration and, on the other hand, an excessively high solids content in the reaction mixture is avoided.

The amount of aluminum chloride added in the process of the invention should be from 1 mol % to 30 mol %, preferably from 5 mol % to 15 mol %, based on the amount of dimethyldichlorosilane used. On the basis of experience, the concentration of $AlCl_3$ should be not less than 5 mol %, since otherwise the reaction comes to a halt at an early stage as a result of the deactivation of the aluminum component and a further addition of aluminum chloride becomes necessary.

Suitable reaction media are alkanes, cycloalkanes, aromatics and alkyl aromatics. Preference is given to using decalin as inert, toxicologically acceptable vehicle since, owing to its high boiling point (bp. 190° C.), it allows the reaction to be carried out within a wide temperature range.

The reduction of the dimethyldichlorosilane is carried out at temperatures of from 50° C. to 200° C.; a temperature curve typical of the reaction results from gradual condensation of the volatile reaction products.

It has been found to be advantageous to combine all reactants before commencement of the reaction. If, as an alternative, dimethyldichlorosilane is added dropwise to the hot mixture of reactants, comprising $MgH_2/AlCl_3$, the premature deposition of an aluminum mirror on the inner wall of the reactor is observed.

The silane mixture obtained from the hydride reduction can be fractionated by distillation, so that, depending on the number of theoretical plates employed, dimethylmonochlorosilane can be isolated in any desired purity.

If the isolation of dimethylmonochlorosilane as such is not necessarily desired, it is possible, for example, to work up the silane mixture hydrolyticallly, forming α,β-bis (hydroxy)polydimethylsiloxane from any dimethyldichlorosilane present by HCl elimination and condensation and tetramethyldisiloxane from dimethylmonochlorosilane by elimination of HCl. Dimethylsilane does not react in neutral to strongly acid medium and can thus be collected separately.

EXAMPLE 1

(Comparative Example)

125 g (1.0 mol) of dimethyldichlorosilane and 27.7 g (1.0 mol) of magnesium hydride (autocatalytically prepared magnesium hydride, hydride content 95%) were suspended in 300 g of decalin and milled in a 500 ml laboratory ball mill at about 1000 rpm.

The reaction mixture was heated and maintained at reflux for 4.5 hours.

No gaseous reaction products could be collected in a downstream low-temperature cold trap.

EXAMPLE 2

(Apparatus Without Condenser)

125 g (1.0 mol) of dimethyldichlorosilane, 13.3 g (0.1 mol) of anhydrous aluminum chloride and 22.2 g (0.8 mol) of magnesium hydride (autocatalytically prepared magnesium hydride, hydride content 95%) were suspended in 250 g of decalin and milled in a 500 ml laboratory ball mill at about 1000 rpm.

While continuing to mill continually, the mixture was heated quickly to 80° C., with the condensation of the evolved gases in a downstream cold trap (−78° C.) being observed.

After a reaction time of about 1.5 hours, a considerable decrease in the condensation rate was observed (95 ml of condensate).

To drive off the residual silane, the reaction temperature was increased, until the reaction was concluded after a further 30 minutes at a final temperature of 120° C.

The condensate obtained (84 g, 95 ml) was, according to $^1H$- and $^{29}Si$-NMR analysis, composed of 53% of dimethylmonochlorosilane as well as 30% of dimethylsilane and 17% of dimethyldichlorosilane. The dimethylmonochlorosilane yield was thus 47 mol % at a dimethyldichlorosilane conversion of 89%.

EXAMPLE 3

129 g (1.0 mol) of dimethyldichlorosilane, 13.3 g (0.1 mol) of anhydrous aluminum chloride and 22.2 g (0.8 mol) of magnesium hydride (autocatalytically prepared magnesium hydride, hydride content 95%) were suspended in 250 g of decalin and milled in a 500 ml laboratory ball mill at about 1000 rpm.

While continuing to mill continually, the mixture was heated quickly to 90° C., with the condensation of the evolved gases in a downstream cold trap (−78° C.) being observed.

After a reaction time of about 3 hours and at a final temperature of 120° C., the reaction was concluded.

The condensate obtained (74 g, 85 ml) was, according to $^1H$- and $^{29}Si$-NMR analysis, composed of 62% of dimethylmonochlorosilane as well as 35% of dimethylsilane and 3% of dimethyldichlorosilane.

The dimethylmonochlorosilane yield was thus 49 mol % at a dimethyldichlorosilane conversion of 92%.

What is claimed is:

1. A process for preparing dimethylmonochlorosilane $(CH_3)_2Si(H)Cl$ comprising establishing a reaction mixture comprising dimethyldichlorosilane $(CH_3)_2SiCl_2$, magnesium hydride, and aluminum chloride, in an inert liquid organic vehicle, and partially hydrogenating said dimethyldichlorosilane in said reaction mixture while milling continually in said liquid organic vehicle.

2. The process as claimed in claim 1, wherein the magnesium hydride is a non-pyrophoric, autocatalytically prepared magnesium hydride.

3. The process as claimed in claim 1 wherein the amount of aluminum chloride in said reaction mixture is from 1 mol % to 30 mol % based on the amount of dimethyldichlorosilane in said reaction mixture.

4. The process as claimed in claim 1 wherein the amount of aluminum chloride in said reaction mixture is from 5 mol % to 15 mol % based on the amount of dimethyldichlorosilane in said reaction mixture.

5. The process as claimed in claim 1 wherein said organic vehicle is selected from the group consisting of cycloalkanes, aromatics and alkyl aromatics.

6. The process as claimed in claim 1 wherein the organic vehicle is decalin.

7. The process as claimed in claim 1 wherein the hydrogenation of the dimethyldichlorosilane is carried out at a temperature of from 50° C. to 200° C.

8. The process as claimed in claim 2 wherein the amount of aluminum chloride in said reaction mixture is from 1 mol % to 30 mol % based on the amount of dimetyldichlorosilane in said reaction mixture.

9. The process as claimed in claim 2 wherein the amount of aluminum chloride in said reaction mixture is from 5 mol % to 15 mol % based on the amount of dimethyldichlorosilane in said reaction mixture.

10. The process as claimed in claim 2 wherein said organic vehicle is selected from the group consisting of cycloalkanes, aromatics and alkyl aromatics.

11. The process as claimed in claim 2 wherein the organic vehicle is decalin.

12. The process as claimed in claim 2 wherein the hydrogenation of the dimethyldichlorosilane is carried out at a temperature of from 50° C. to 200° C.

* * * * *

UNITED STATES PATENT AND TRADEMARK OFFICE
CERTIFICATE OF CORRECTION

PATENT NO. : 5,856,548
DATED : January 5, 1999
INVENTOR(S) : Jurgen Drose, et al.

It is certified that error appears in the above-identified patent and that said Letters Patent are hereby corrected as shown below:

Column 3, Line 36: "hydrolyticallly" should read --hydrolytically--

Column 3, Line 36: "$\alpha, \beta$-bis" should read --$\alpha, \omega$-bis--

Column 3, Line 40: "HC1" should read --HCl--

Column 4, Lines 63 and 64, Claim 8: "dimetyldichlorosilane" should read --dimethyldichlorosilane--

Signed and Sealed this

First Day of May, 2001

Attest:

NICHOLAS P. GODICI

Attesting Officer          Acting Director of the United States Patent and Trademark Office